(12) United States Patent
Hassan et al.

(10) Patent No.: US 11,266,329 B2
(45) Date of Patent: Mar. 8, 2022

(54) ENERGY HARVESTING FOR SENSOR SYSTEMS

(71) Applicant: NATIONAL ICT AUSTRALIA LIMITED, Eveleigh (AU)

(72) Inventors: Mahbub Hassan, Eveleigh (AU); Wen Hu, Eveleigh (AU); Sara Khalifa, Eveleigh (AU); Aruna Seneviratne, Eveleigh (AU)

(73) Assignee: NATIONAL ICT AUSTRALIA LIMITED, Eveleigh (AU)

( * ) Notice: Subject to any disclaimer, the term of this patent is extended or adjusted under 35 U.S.C. 154(b) by 0 days.

(21) Appl. No.: 16/084,729

(22) PCT Filed: Mar. 14, 2017

(86) PCT No.: PCT/AU2017/050225
§ 371 (c)(1),
(2) Date: Sep. 13, 2018

(87) PCT Pub. No.: WO2017/156577
PCT Pub. Date: Sep. 21, 2017

(65) Prior Publication Data
US 2019/0076061 A1 Mar. 14, 2019

(30) Foreign Application Priority Data
Mar. 14, 2016 (AU) .............................. 2016900940

(51) Int. Cl.
*A61B 5/117* (2016.01)
*A61B 5/00* (2006.01)
(Continued)

(52) U.S. Cl.
CPC ............ *A61B 5/117* (2013.01); *A61B 5/0002* (2013.01); *A61B 5/112* (2013.01); *A61B 5/1118* (2013.01);
(Continued)

(58) Field of Classification Search
CPC ..... A61B 5/117; A61B 5/0002; A61B 5/1118; A61B 5/112; A61B 2560/0242; G06F 19/00; H04L 4/1136; H02N 2/181
See application file for complete search history.

(56) References Cited

U.S. PATENT DOCUMENTS 8,387,468 B2 3/2013 Hughes et al.
8,652,040 B2 2/2014 LeBoeuf et al.
(Continued)

FOREIGN PATENT DOCUMENTS

CN 104732186 A 6/2015
CN 104970489 A 10/2015
(Continued)

OTHER PUBLICATIONS

Li, Y., Ngom, A. Sparse representation approaches for the classification of high-dimensional biological data. BMC Syst Biol 7 , S6.*
(Continued)

*Primary Examiner* — Zhitong Chen
(74) *Attorney, Agent, or Firm* — Ladas & Parry LLP

(57) ABSTRACT

Described is an energy harvesting system comprising a transducer that generates an electric signal from ambient energy, and a processor adapted to process the electric signal to determine and output a characteristic of a source of the ambient energy. The characteristic may be a spoken word classification.

12 Claims, 9 Drawing Sheets

(51) Int. Cl.
  *A61B 5/11*  (2006.01)
  *H01L 41/113*  (2006.01)
  *H02N 2/18*  (2006.01)
  *G16Z 99/00*  (2019.01)

(52) U.S. Cl.
  CPC .......... *G16Z 99/00* (2019.02); *H01L 41/1136* (2013.01); *H02N 2/181* (2013.01); *A61B 2560/0242* (2013.01)

(56) References Cited

U.S. PATENT DOCUMENTS

| | | | |
|---|---|---|---|
| 2008/0146890 A1* | 6/2008 | LeBoeuf | A61B 5/4839 600/300 |
| 2011/0224915 A1* | 9/2011 | Hughes | A61B 5/0002 702/19 |
| 2013/0157729 A1 | 6/2013 | Tabe | |
| 2017/0035327 A1* | 2/2017 | Yuen | A61B 5/11 |
| 2017/0055880 A1* | 3/2017 | Agrawal | A61B 5/7405 |
| 2017/0299426 A1* | 10/2017 | Lee | G10L 21/028 |

FOREIGN PATENT DOCUMENTS

| | | |
|---|---|---|
| CN | 105046193 A | 11/2015 |
| CN | 105224918 A | 1/2016 |

OTHER PUBLICATIONS

Huang, Ke, and Selin Aviyente. "Sparse representation for signal classification." Advances in neural information processing systems 2007.*

International Search Report (ISR) and Written Opinion (WO) dated Jun. 1, 2017 for International Application No. PCT/AU2017/050225.

Chinese office action dated Oct. 15, 2021 for Application No. CN 201780028186.3 (English Translation).

Espacenet English abstract of CN 104970489 A.
Espacenet English abstract of CN 105046193 A.
Espacenet English abstract of CN 104732186 A.
Espacenet English abstract of CN 105224918 A.

* cited by examiner

ENERGY HARVESTING FOR SENSOR SYSTEMS

RELATED APPLICATION

This application is a national phase entry under 35 USC 371 of International Patent Application No.: PCT/AU2017/050225 filed on 14 Mar. 2017, which claims priority from AU application No. 2016900940 filed on 14 Mar. 2016 the entire contents of which are incorporated herein by reference.

TECHNICAL FIELD

This disclosure relates to the use of energy harvesting for human activity recognition.

BACKGROUND

One of the challenges in sensor systems is meeting the power requirements where the systems are wireless or rely on batteries. One possible solution for sensor systems deployed within a suitable context that lends itself to energy harvesting, is to harvest energy from the system environment and to use this harvested energy to contribute to the power used for the sensor system. Energy can be harvested from a number of different sources, such as solar power, thermal energy (or temperature gradients), wind energy, electromagnetic energy, salinity gradients and kinetic energy from movement or vibration.

One example of this is in wearable technology, such as activity-aware services that make use of human activity recognition (HAR) in various domains like healthcare and indoor positioning. Battery life is a problem with wearable HAR technology so that wearables therefore either need large batteries or the batteries must be charged regularly in order to achieve sustained operation.

Using energy harvesting has been considered for providing power for wearable HAR technology, however the amount of energy that can be harvested is generally small in comparison to the power requirements of the HAR application.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Conventional sensor systems typically have (1) a sensing component that provides sensed data, (2) a processor for extracting data from the sensed data, and (3) a component for distributing the sensed and/or processed data (e.g. memory or a transmitter). A power source that provides power for all three of these components of the system is required. If the power source relies (either wholly or in part) on harvested energy for the power supply then it would be beneficial to reduce the power requirements of one or more of the three components.

One way of doing this is to remove the sensing component by incorporating the sensing functionality into a transducer used for energy harvesting.

In one aspect there is provided an energy harvesting system comprising:
a transducer that generates an electric signal from ambient energy; and
a processor adapted to process the electric signal to determine and output a characteristic of a source of the ambient energy, wherein the characteristic is a spoken word classification.

The ambient energy may be kinetic or vibration energy generated by an activity, and the transducer may be a kinetic energy harvester such as a piezoelectric transducer.

The kinetic energy harvester may comprise two or three orthogonal transducers providing multi-axial electric signals that comprise identifying features associated with directions of the activity.

The piezoelectric transducer may have a cantilevered beam configuration, and may have a substantially horizontal orientation.

In another aspect there is provided an energy harvesting system comprising:
a transducer that generates an electric signal from ambient energy; and
a processor adapted to process the electric signal to determine and output a characteristic of a source of the ambient energy, wherein the characteristic may be associated with a user's gait and is indicative of a user's identification. The processor may determine the characteristic by determining a minimal residual of a weighted summation of test vectors in a sparse representation.

In another aspect there is provided a method comprising:
receiving and transforming ambient energy into an electrical signal;
processing the electrical signal to extract at least one distinguishing feature;
classifying a source of the ambient energy based on the at least one distinguishing feature; and
outputting the classification, wherein classification may be a spoken word classification.

The receiving and transforming may be done with a kinetic energy harvester, and the kinetic energy harvester may be a piezoelectric transducer. The ambient energy may be kinetic or vibration energy.

The piezoelectric transducer may have a cantilevered beam configuration, and may have a substantially horizontal orientation.

In another aspect there is provided a method comprising:
receiving and transforming ambient energy into an electrical signal;
processing the electrical signal to extract at least one distinguishing feature;
classifying a source of the ambient energy based on the at least one distinguishing feature; and
outputting the classification,
wherein the classification is based on a user's gait and is indicative of a user's identification. The classifying may comprise determining a minimal residual of a weighted summation of test vectors in a sparse representation.

As used herein, except where the context requires otherwise, the term "comprise" and variations of the term, such as "comprising", "comprises" and "comprised", are not intended to exclude further additives, components, integers or steps.

DESCRIPTION OF EMBODIMENTS

Conventional systems used for determining characteristics of movement, e.g. to provide activity-aware services such as in wearable HAR systems, typically make use of accelerometers to obtain data about the activities. However, the power requirement of accelerometers is significant, and has been shown to range between 0.35 and 5 times the harvested kinetic energy when detecting common human activities (e.g. walking and running). Some activities generate only a few μW, not enough to power both an accelerometer and radio communication required to transmit the sensed data. The same is true for other remote sensing activities, e.g. when sensing movement or vibrations on buildings. Similarly, if energy is harvested from another source, e.g. temperature or solar energy, the same is true when sensing related parameters with a dedicated sensor, such as temperature.

Figure 1:
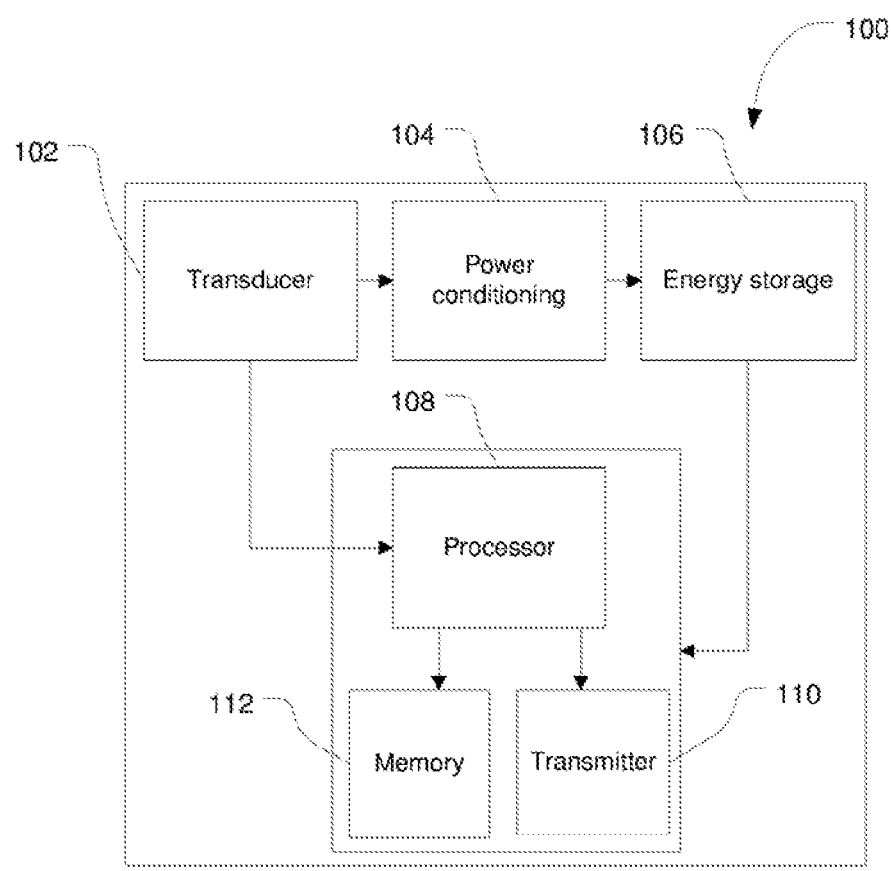
FIG. 1 is a schematic representation of a system for identifying the source of ambient energy.

FIG. 1 is a schematic representation of a system 100 for identifying an activity that uses kinetic energy harvesting and does not use an accelerometer. Instead of using an accelerometer to obtain data about the activity, a transducer 102 harvests ambient energy and the power generated from the harvested energy provides information about the activity.

In this embodiment the transducer 102 is a piezoelectric transducer with a cantilevered beam configuration. When the piezoelectric material is subjected to a mechanical stress due to any source of environmental vibrations, it expands on one side and contracts on the other. Positive charges accumulate on the expanded side and negative charges on the contracted side, generating an AC voltage as the beam oscillates around the neutral position. The amount of voltage is proportional to the applied stress, which means that different vibration patterns would generate different AC voltage patterns. An example of a piezoelectric KEH transducer is the MIDE Volture transducer.

The AC output of the transducer is rectified and regulated by a power conditioning circuit 104 so that it can be stored in the energy storage 106 (a battery or capacitor) as DC voltage used to power the processor 108 and transmitter 110. Power regulation may include analogue to digital conversion. The stored energy may be used to fully or partially power the processor 108, memory 112, and/or transmitter 110.

The regulated power is may not be suitable for detecting features in the electric signal produced by the transducer because regulation removes potential patterns from the signal. In the system shown in FIG. 1, the AC voltage produced by the transducer is used by the processor 108 to determine the source of the ambient energy. In this example the source of the ambient energy means recognising the activity performed by a user resulting in the kinetic energy that is harvested.

The activity identifier (i.e. walking, standing, running, ascending or descending stairs, vacuuming, going up/down an escalator, walking/running up a ramp, walking/running down a ramp, etc.) may be stored in memory 112 and/or transmitted to another system or processor via the transmitter 110.

Figure 2:
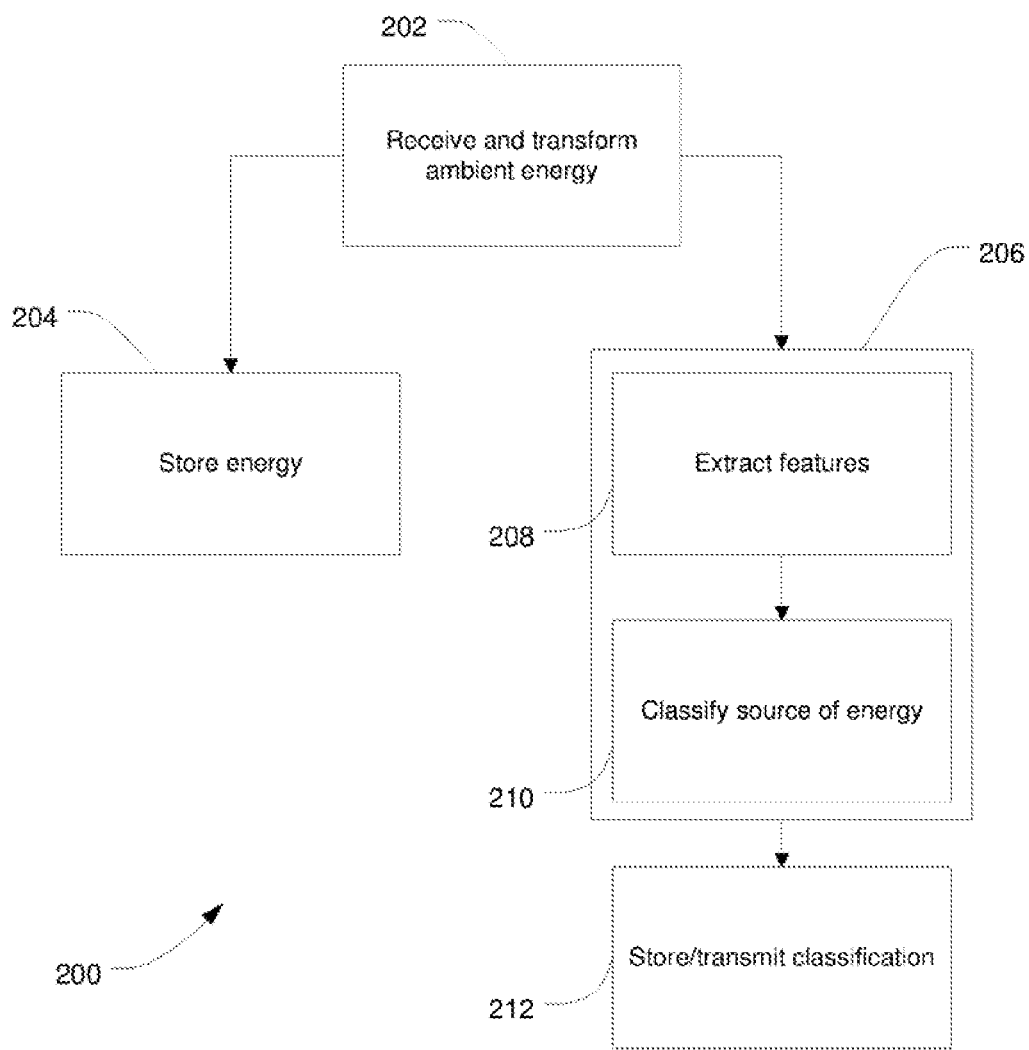
FIG. 2 is a flow diagram of a method for identifying the source of ambient energy.

The process 200 used to determine the activity identifier may be understood with reference to FIG. 2.

The transducer 102 receives and transforms ambient energy 202, in this example kinetic energy. The resulting power is stored 204 over a period of time in the energy storage 104 (e.g. a capacitor or battery), and this step may include rectifying and regulating the electric signal output by the transducer.

The unprocessed electric signal output from the transducer is then processed 206 by the processor 108. This includes first extracting features 208 from the electric signal. These may be any combination of distinguishing features that describe the data, for example the root mean square, peak-to-peak value, peak-to-peak difference, mean peak, mean peak distance, maximum peak, maximum peak distance, mean, variance, standard deviation, minimum, maximum, range, absolute mean, coefficient of variation, skewness, kurtosis, quartiles, inter quartile range, mean crossing rage, absolute area, dominant frequency, dominant frequency ratio, energy, frequency domain entropy, mean absolute deviation, auto-correlation, power spectrum mean.

Some of these are described in Table 1 below.

TABLE 1

An example feature set used to analyse the source of harvested ambient energy

| | | Feature | Abbreviation | Description |
|---|---|---|---|---|
| Single axis features | Time-domain features | mean | mean | the central value of a window of samples. |
| | | variance | var | a measure the amount of variation or dispersion from the mean. |
| | | standard deviation | std | the square root of the variance. |
| | | minimum | min | the minimum value in a window of samples |
| | | maximum | max | the maximum value in a window of samples |
| | | range | range | the difference between the maximum and the minimum values in a window of samples |
| | | Absolute Mean | absMean | average of absolute values, |
| | | Coefficient of Variation | CV | ratio of standard deviation and mean times 100; measure of signal dispersion, |
| | | Skewness | skew | measure of asymmetry of the probability distribution of the window of samples, |
| | | Kurtosis | kurt | measure of peakedness of the probability distribution of the window of samples, |

TABLE 1-continued

An example feature set used to analyse the source of harvested ambient energy

| | Feature | Abbreviation | Description |
|---|---|---|---|
| | Quartiles:<br>1st Quartile:<br>2nd Quartile<br>3rd Quartile | Q1<br>Q2<br>Q3 | measures the overall distribution of the signal samples over the window, |
| | Inter Quartile Range | IQR | the difference between the upper (third) quartile and the lower (first) quartile of the window of samples; also measures the dispersion of the signal samples over the window, |
| | Mean Crossing Rate | MCR | measures the number of times the signal crosses the mean value; captures how often the signal varies during the time window, |
| | Absolute Area | absArea | the area under the absolute values of the signal samples. It is the sum of absolute values of the signal samples over the window, |
| Frequency-domain features | Dominant Frequency Ratio | DFreqR | it is calculated as the ratio of highest magnitude FFT coefficient to sum of magnitude of all FFT coefficients. |
| | Energy | FDEnergy | it is a measure of total energy in all frequencies. It is calculated as the sum of the squared discrete FFT component magnitudes. |

$$\text{Energy} = \sum_{i=1}^{L/2} F_i^2 \qquad (4.3)$$

where $F_i$ is the magnitude of FFT coefficients.

| | Entropy | FDEntropy | captures the impurity in the measured data. It is calculated as the information entropy of the normalized values of FFT coefficient magnitude. |
|---|---|---|---|

$$\text{Entropy} = -\sum_{i=1}^{L} Fn_i \log_2(Fn_i) \qquad (4.4)$$

where $Fn_i$ is the normalized value of FFT coefficient magnitude.

More particularly, it has been found that features that are particularly useful when harvesting kinetic energy with a piezoelectric KEH are the ones shown in the feature set in Table 2 below.

TABLE 2

A "Vibration Feature Set" (VFS) used to extract features from KEH data

| Feature | Abbreviation | Description |
|---|---|---|
| root mean square | RMS | it is the square root of the arithmetic mean of the square of the values. The RMS is a measurement of the effective energy content in a the signal. |
| peak-to-peak | PktPk | it is the difference between the maximum peak value and the minimum peak value. It indicates the maximum excursion of the signal. |
| peak-to-peak difference | PktPkDiff | The difference between the maximum difference between peak values and the minimum difference between peak values of the sinusoidal wave. It indicates the maximum excursion of the time periods. |
| mean Peak | meanPk | The mean value of the differences between all the peak values. It quantifies the average variation level of the values of the signal. |
| mean Peak Distances | meanDisPk | The mean value of the differences between the all the distances (time periods) between peak values. It quantifies the average variation level of the time periods of the signal. |
| maximum Peak | maxPk | The maximum value of the differences between all the peak values. It quantifies the maximum variation level of the time periods of the signal. |
| maximum Peak Distance | maxDisPk | The maximum value of the differences between all the distances (time periods) between peak values. It quantifies the maximum variation level of the time periods of the signal. |

The kinetic energy harvester may comprise two or three orthogonal transducers providing multi-axial electric signals that comprise identifying features associated with directions of the activity. In such embodiments, the feature set used may include features particular to multi-axial data, as shown in Table 3.

TABLE 3

Multi-axial feature set

| multiaxes features | Time-domain features | Total absolute area | TAA of the three axes the absolute area of all three axis. |
|---|---|---|---|

$$\text{totalAA} = \sum_{i=1}^{L} |Acc_x| + |Acc_y| + |Acc_z| \qquad (4.5)$$

where $|Acc_x|$, $|Acc_x|$, and $|Acc_x|$ are the absolute values of the three axes x, y, and z respectively. L is the length of the window.

| | | total magnitude area | MMA | the signal magnitude of the three axes averaged over the time window. |
|---|---|---|---|---|

$$\text{totalMA} = \frac{\sum_{i=1}^{L} \sqrt{Acc_x^2 + Acc_y^2 + Acc_z^2}}{L} \qquad (4.6)$$

| | | Correlation Corr(X,Y) Corr(X,Z) Corr(Y,Z) | CorrXY CorrXZ CorrYZ | it measures the dependence relationship between two axes |
|---|---|---|---|---|

Following feature extraction 208, the data is classified 210 according to one of the identifiers, e.g. kinetic energy may have been harvested from one of walking, running, standing, ascending or descending stairs, etc. Classification 210 is performed using a suitable known method, such as Decision Tree (DT), K-Nearest Neighbour (KNN), Multi-layer Perceptron (MLP), Support Vector Machine (SVM), or Naïve Bayes (NB).

The outcome of the identification process 206 is then output 212 according to the particular application. For example, where a wearable is used for continuous HAR then the output maybe stored in memory on the wearable for later retrieval (e.g. in wired communication with a computer), the output may be displayed on the wearable device, or the output may be transmitted with wireless communication to another processor or computer.

It has been found that, with an appropriate feature set (e.g. as shown in Table 2), and an appropriate classifier (e.g. KNN), accuracy of up to 83% can be obtained in HAR. This can be improved even further depending on the placement of the transducer, e.g. handheld, on a wrist, on the waist, hip or at the knee. For example, moving the transducer from a handheld position to a waist position resulted in an average improvement of accuracy from 83% to 87%. By eliminating the accelerometer that is typically used in HAR systems, a power saving of 70-80% in comparison to conventional systems may be achieved.

The processing 206 may include determining other information from the electric signal, for example for use in health monitors or as described below with reference to the examples presented as described below with reference to the examples presented.

Example 1—Step Count

Characteristics of harvested energy can be used to detect steps in human motion and provide a step count as an output. One method for doing this uses a peak detection algorithm. Because of the irregularity of human movements and also hardware noise, not all detected peaks are valid steps. Peaks that are unlikely to be associated with steps and that are to be avoided in determining step count can be avoided by the use of two thresholds: $T_1$ is the minimum peak height, and $T_2$ is the minimum distance between every two consecutive peaks. Using these thresholds, the peaks that represent valid steps are only those peaks higher than $T_1$ and separated by at least $T_2$. Using peak detection, step count using this method has been shown to have an accuracy of up to 96%.

Figure 3A:
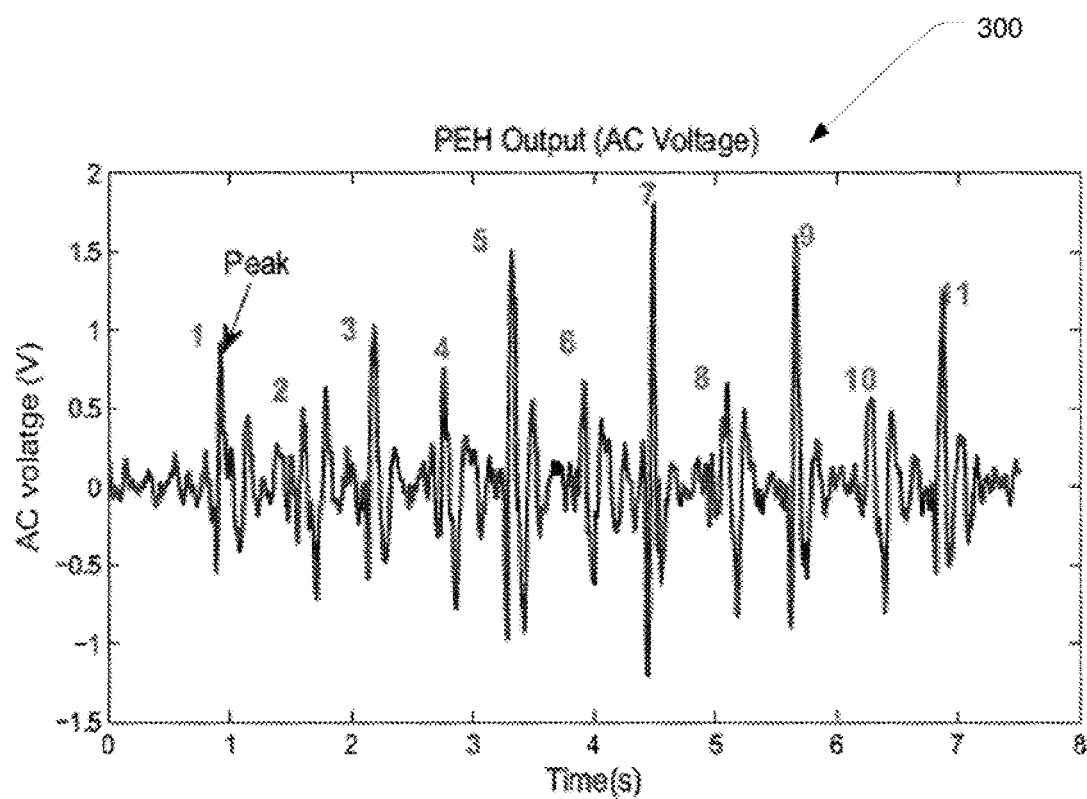
FIG. 3a is the voltage output from a piezoelectric energy harvester (PEH) where the voltage peaks accord with the step count.

The peak height threshold $T_1$ and the step distance threshold $T_2$ may be determined from the data collected using machine learning, or may be selected based on a predetermined value. For example, referring to FIG. 3a, $T_1$=0.2V and $T_2$=0.4 ms for the example voltage output 300 that is output from the transducer.

In addition to this peak detection algorithm, step count can also be determined using a zero crossing detection algorithm or a moving variance detection algorithm.

Example 2—Calorie Expenditure

Caloric expenditure may be estimated by incorporating anthropometric features (e.g. height, age, weight) together with the electric signal in a regression model. The anthropometric features are input by the user and the linear regression model is trained, e.g. using indirect calorimeters to provide a calorie expenditure estimate (CEE). A suitable regression model may be represented as follows:

$$\overline{\text{CEE}}_{volt} = X\beta + \varepsilon$$

where $\overline{\text{CEE}}_{volt}$ indicates the estimated calorie expenditure at the kth minute. X denotes the vector of input signals, including the anthropometric features of the subjects, and the output voltage signals from the energy harvester. The $\beta$ and $\varepsilon$ are the vectors of coefficients and residual error, respectively. It has been shown that the average (over one second or longer) CEE achieved using harvested energy compares well with conventional methods using accelerometers.

Example 3—Hotword Detection

Piezoelectric transducers are also used to harvest energy from vibration energy: vibration energy harvesting (VEH). Analogous to the preceding examples, the harvested energy can be used to determine characteristics of the source of the vibration energy.

Hotwords, such as "OK Google" are used by voice control applications to distinguish user commands from background conversations. Pervasive hotword detection requires continuous sensing of audio signals, which results in significant energy consumption when a microphone is used as an audio sensor.

Using VEH in a personal mobile device for hotword detection may therefore contribute to a reduction in power consumption.

A piezoelectric transducer with a cantilevered beam configuration is used to harvest vibration energy. The piezoelectric material is subjected to mechanical stress due to environmental vibrations, resulting in the generation of an AC voltage proportional to the applied stress. Consequently different vibration patterns result in different AC voltage patterns.

Figure 3B:
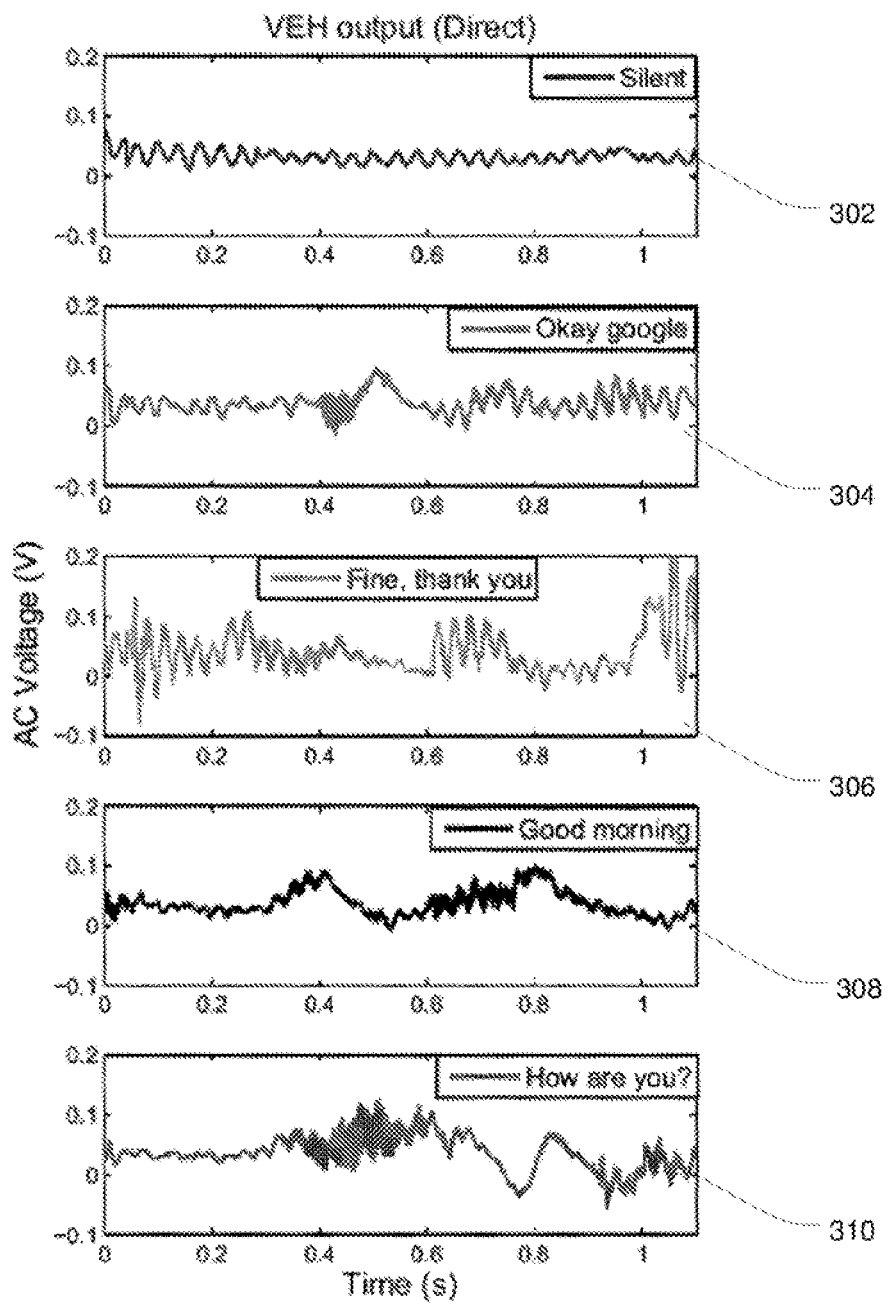
FIG. 3b shows hotword detection examples of transducer voltage outputs for different spoken phrases.

Human speech creates sound waves that cause piezoelectric transducers to generate different AC voltage patterns for different words and phrases. FIG. 3b shows a number of these AC voltage patterns for the proposed system. The silent voltage pattern 302 is a generally small oscillation close to 0V while each of the spoken phrases considered show a distinctive pattern: "Okay Google" 304, "Fine, thank you" 306, "Good morning" 308 and "How are you?" 310.

Once the vibration energy has been received and transformed into electrical energy the data is processed to extract features. One or more features, e.g. from Table 1 may be used, for example the subset shown in Table 2. Classification is performed, e.g. using a Decision Tree (DT) classifier that has been trained by a number of test phrases (e.g. those shown in FIG. 3b). Features are tested and selected that have the most inhomogeneous class distribution based on the information gain (G). The IG of feature measures the expected reduction in entropy caused by partitioning the data according to this feature. The calculation of information gain is based on calculating the entropy H(S) of a set of classes S. The information gain is then calculated using:

$$\text{Gain}(S, f_i)H(S) - \sum_{v \in \text{Values}(f_i)} \frac{|S_v|}{|S|} H(S_v)$$

where $S_v$ is the subset of S for which feature $f_i$ has a value v and |S| denotes the cardinality of the set S.

Figure 4A:
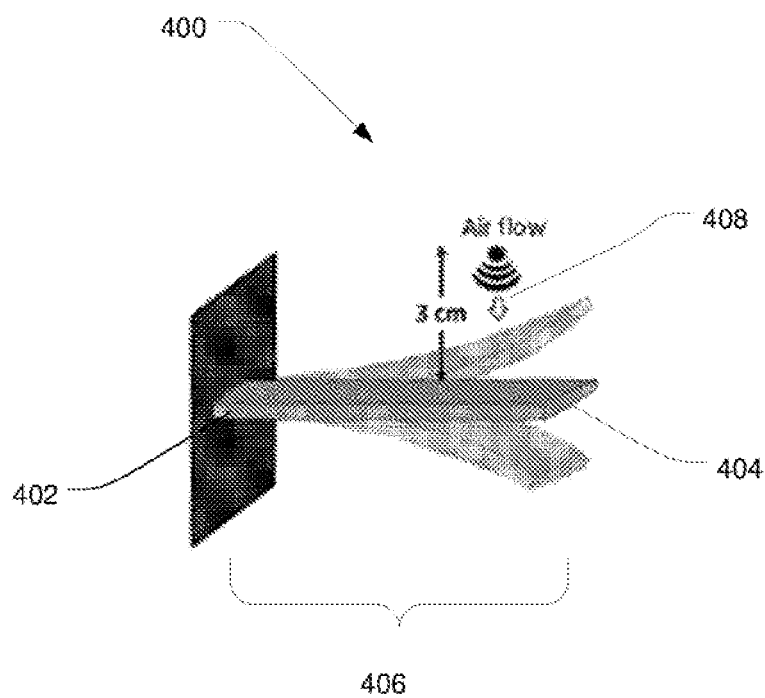
FIGS. 4a and 4b show a horizontal and a vertical transducer orientation, respectively.
Figure 4B:
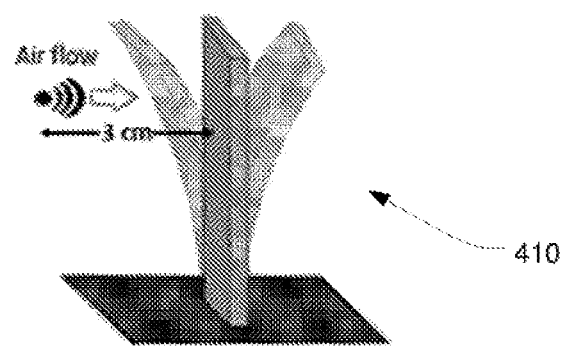

Using this method, hotword detection accuracy of up to 85% has been achieved. The best results are achieved with the correct orientation of the cantilevered beam of the transducer. Consider a horizontal cantilevered beam piezoelectric transducer 400 as shown in FIG. 4a. As used here, the terms horizontal and vertical are in relation to ground. The transducer 400 has one end 402 fixed, a free end 404 that is caused to move by ambient vibration or kinetic energy, and a flat portion 406 of the beam between these two ends 402, 404. If the direction of air flow is towards the flat portion 406 of the beam as shown by arrow 408 there is a marked improvement in the results when compared to randomly directed speech. In addition, the horizontal transducer 400 provides better results than the vertically oriented transducer 410 shown in FIG. 4b. Therefore, to improve the accuracy, in some embodiments the transducer is built into a mobile device so that it is generally horizontally oriented when the mobile device is in an upright position (or when the mobile device is oriented in a way that the device is typically used). In other embodiments VEH is performed with a multi-axial configuration of two or more transducers at different orientations, for example three orthogonal transducers.

Example 4—Gait Recognition

Figure 5A:
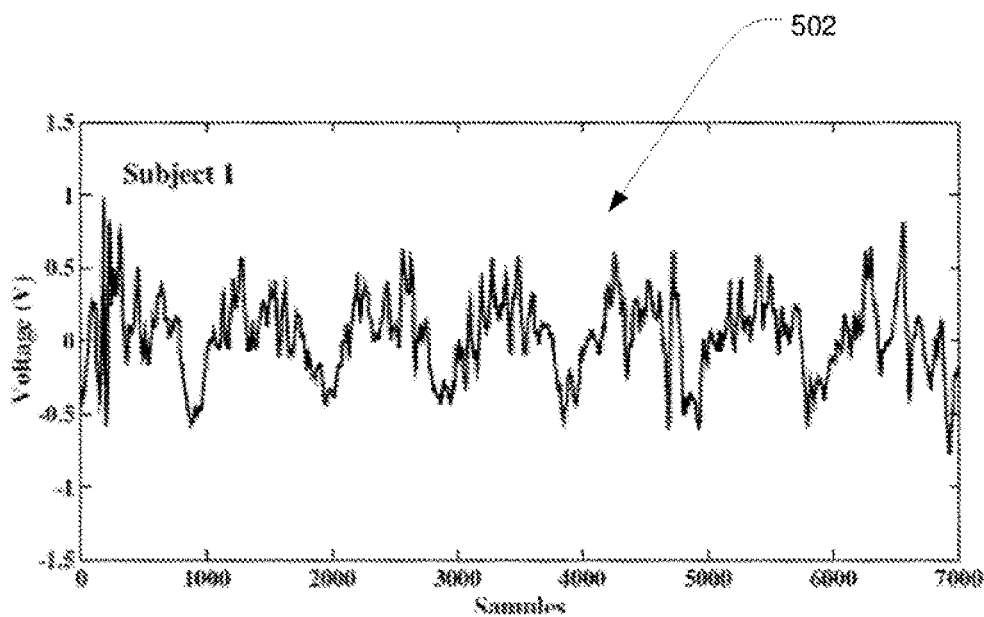
FIGS. 5a and 5b show gait detection examples of transducer voltage outputs for different users.
Figure 5B:
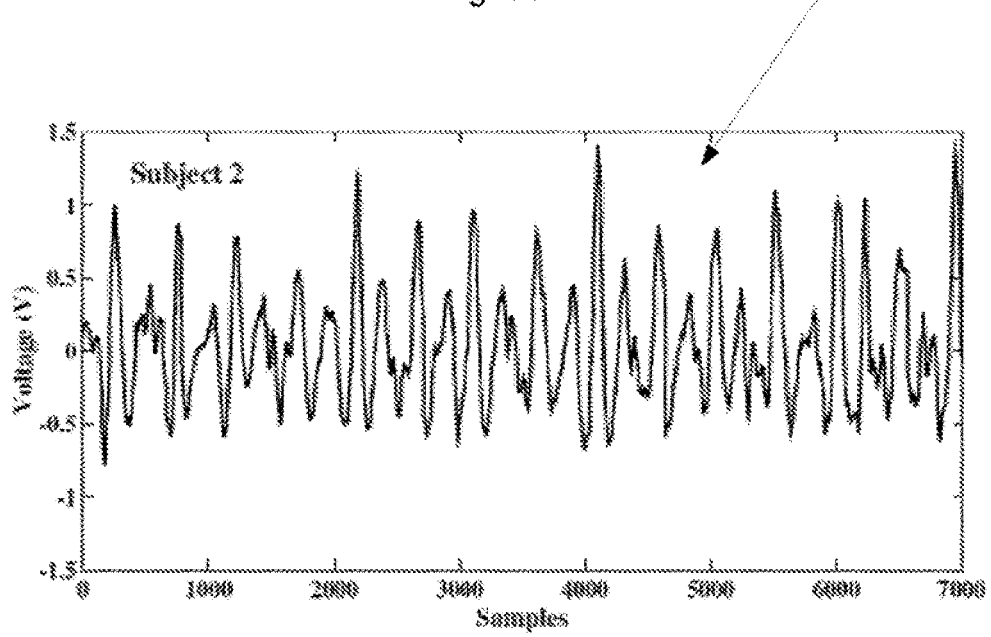

Gait recognition refers to the automatic recognition of individuals based on their walking patterns. Different people produce kinetic energy in a personalised way, providing distinctive patterns that can be used for gait-based user authentication. This can be seen in FIGS. 5a and 5b which show voltage signals 502, 504 from a piezoelectric transducer for two different people when they are walking.

Figure 6:
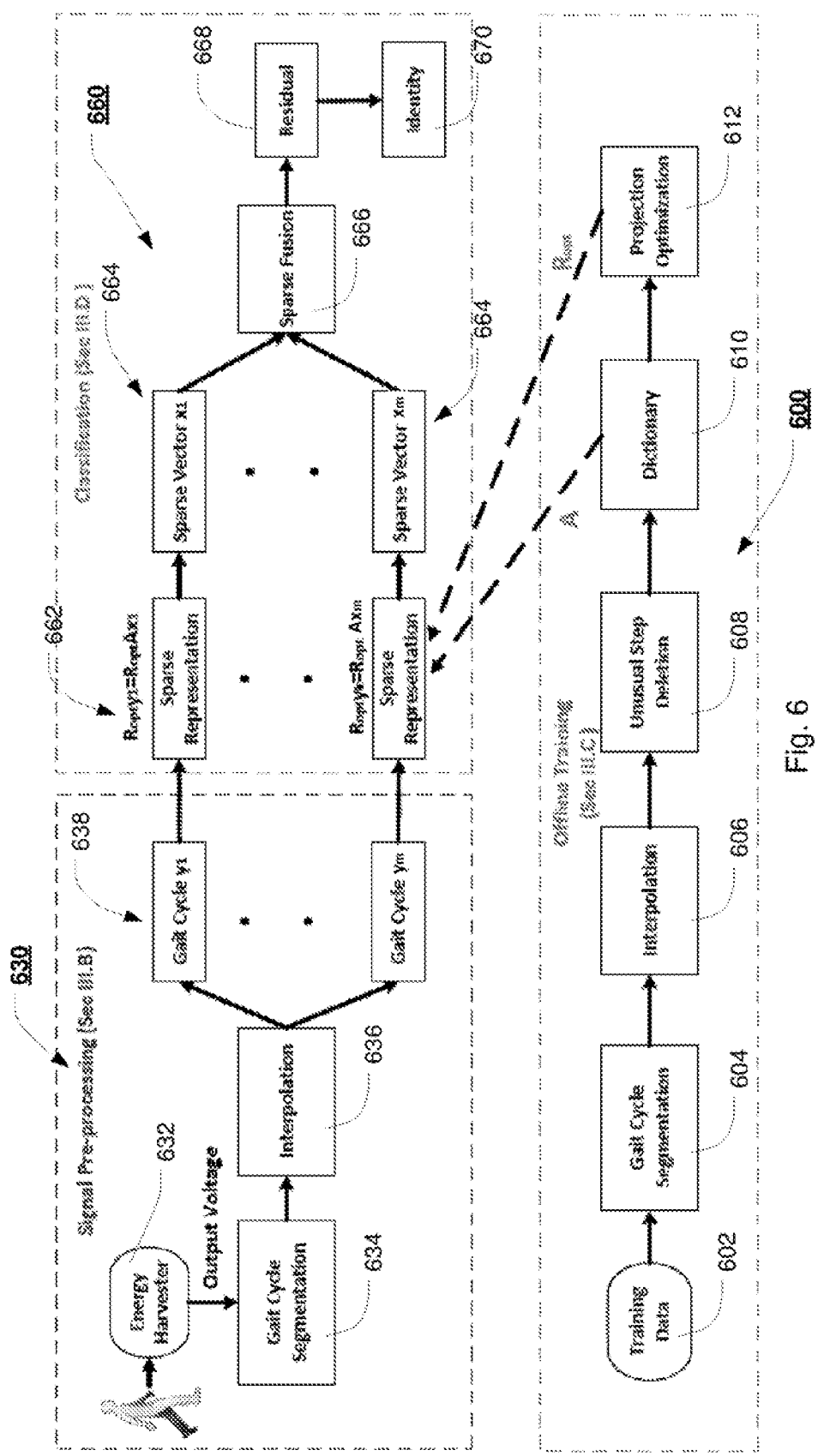
FIG. 6 is an overview of a gait-based user authentication method.

FIG. 6 shows an overview of the signal processing applied for gait-based user authentication. The three main stages shown are the offline dictionary training 600, signal pre-processing 630, and classification 660.

Offline Training 600

Figure 7A:
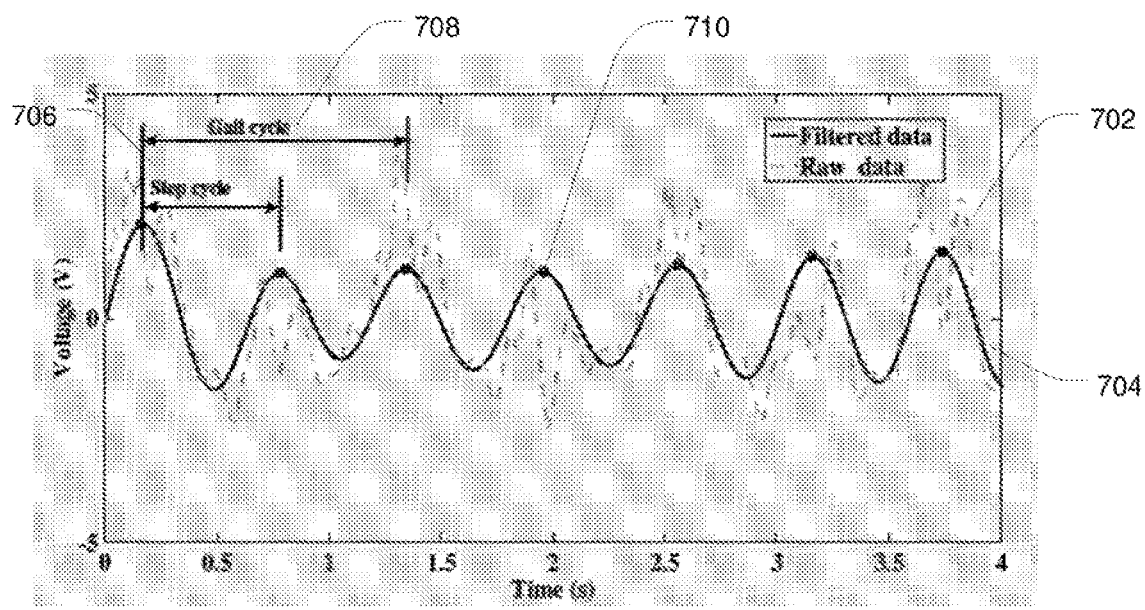
FIG. 7a illustrates step and gait cycles.

During the offline dictionary training 600, the raw training data 602 is provided and gait cycles are segmented 604. This may be understood with reference to FIG. 7a. One gait cycle (one stride) is a combination of two successive step cycles (two steps). A typical step frequency is between 1 and 2 Hz, so that a simple bandpass filter applied to the unfiltered voltage signal 702 provides a filtered signal 704. Heal strikes are associated with the peaks 710 in the filtered signal so that a clear indication of step cycles 706 and gait cycles 708 is provided by the filtered signal 704. A typical range for gate cycles is between 0.8 and 1.3 s, and gait cycles outside of this range are removed from the training data.

The classification method used in this example is Sparse Representation Classification (SRC), described below. Because SRC requires vectors of equal length, linear interpolation 606 is used to expand all the gate cycles to the same length, e.g. 1.3 s (or 1300 samples at 1000 Hz sampling rate).

Outliers or unusual cycles (such as temporary walking pauses or turning) are also removed 608 from the training data with the use of Dynamic Time Warping (DTW) distance scores. After unusual cycles have been removed, the remaining gait cycles are used to form the final training dictionary 610. A, with the use of SRC.

In one embodiment, a heuristic algorithm is used to find the optimal projection matrix 612, $R_{opt}$. $R_{opt}$ is also determined during offline training 600, and is used to cast the residual calculation to a lower dimensionality, thereby simplifying the required calculation.

Sparse Representation Classification (SRC) and the Optimised Projection Matrix $R_{opt}$ SRC is a classification algorithm used for pattern recognition. The SRC method solves a single-label classification problem that aims to return the class that best matches a given test sample.

STEP 1—The first step is to build a dictionary A consisting of training vectors from different classes. SRC is applied to:

$$y = Ax \qquad (1)$$

where $y \in \mathbb{R}^q$, $A \in \mathbb{R}^{q \times (N \cdot K)}$ is the dictionary consisting of K classes and each class contains N q-dimensional training vectors.

STEP 2—In the next step, $l_1$ optimisation (where sparse solutions are found by solving an optimisation problem involving an $l_1$-norm) is used to solve (1) with the following sparse assumption:

$$\hat{x} = \arg\min_{x} \|x\|_1 \quad \text{subject to } \|y - Ax\|_2 < \epsilon \tag{2}$$

where $\epsilon$ is used to account for noise and the sparse assumption holds when the test vector can be represented by one of the classes in A.

STEP 3—In preparation for determining the residual in the next step, the coefficients vector $\delta_i(\hat{x})$ is required. After solving the optimisation problem shown in equation (2), a vector of optimal solutions is found: $\hat{x}$. $\delta_i(\hat{x})$ contains the coefficients related to class i only, and the coefficients related to other classes are set to zero.

STEP 4—The residual for class i is then determined, and the correct class produces the minimal residual.

In one embodiment, a random projection matrix is applied to the $l_1$ optimisation. The projection matrices are randomly generated (from Bernoulli or Gaussian distributions that preserve information). The sparse representation vector is then given by:

$$\hat{x} = \arg\min_{x} \|x\|_1 \quad \text{subject to } \|Ry - RAx\|_2 < \epsilon \tag{3}$$

After obtaining the sparse representation vector x the class results are determined by checking the residuals based on the Euclidian distance. In this method the residual for class i is:

$$r_i(y) = \|y - A\delta_i(\hat{x})\|_2 \tag{4}$$

where $\delta_i(\hat{x})$ contains the coefficients related to class i. The correct class produces the minimal residual so that the final result of the classification is:

$$\hat{i} = \arg\min_{i=1,\ldots,K} r_i(y) \tag{5}$$

In another embodiment, a heuristic algorithm is used to find the optimal projection matrix instead of the random one. The compressed residual determined in STEP 4 as described above is then given by:

$$r_i(y) = \|R_{opt}y - R_{opt}A\delta_i(\hat{x})\|_2 \tag{6}$$

where $R_{opt} \in \mathbb{R}^{p \times q}$ is the optimised projection matrix which is output from the offline training 600 and subsequently used during classification 660, described below.

Signal Pre-Processing 630

During signal pre-processing 630 the kinetic energy harvester (KEH) 632 provides an output voltage that is pre-processed using gait cycle segmentation 634 and interpolation 636 similar to the segmentation 604 and interpolation 606 methods described above with reference to the offline training 600. The resulting gait cycles 638 $y_1$ to $y_m$ are output for classification 660.

Classification 660

Classification 660 may be implemented using a number of appropriate classification algorithms such as Support Vector Machine (SVM), K-Nearest Neighbour (KNN) or Naïve Bayes. However, it has been found that the sparse fusion model described below provides the best results in terms of accuracy.

The proposed sparse fusion model fuses the sparse coefficients vectors from multiple consecutive gait cycles to improve recognition accuracy. The sparse fusion model is based on the assumption that one person's consecutive gait cycles tend to have a high agreement with the sparse representations 662 (as obtained by using the optimal projection matrix) because each of the gait cycles from the same person should be linearly represented by the same class in the dictionary.

In the example shown the set of M gait cycles 638 have been acquired from the test signal, and the set of estimated coefficients vectors $\hat{X} = \{\hat{x}_1, \hat{x}_2, \ldots, \hat{x}_M\}$ 664 is obtained by solving the $l_1$ optimization problem for each gait cycle when the sparse representation 662 is determined.

Theoretically, a precise sparse representation will only contain the non-zero entries at the locations related to the specific class. However, noise exists in the empirical estimations. Therefore, the estimated coefficients vector of the m-th test gait cycle can be expressed as:

$$\hat{x}_m = x + \epsilon_m \tag{7}$$

where x is the theoretical sparse representation of the test vector and $\epsilon_m$ is used to account for noise.

The test vector could be misclassified due to low Signal to Noise Ratio (SNR). To enhance the SNR of the classification system, the new sparse representation model is used and it exploits the information from multiple gait cycles. The new sparse representation model can be expressed as:

$$\hat{x}_{sum} = \sum_{m=1}^{M} \alpha_m \hat{x}_m \tag{8}$$

where $\alpha_m$ is the weight assigned to $\hat{x}_m$ based on a Sparsity Concentration Index (SCI) which is defined as:

$$SCI(\hat{x}_m) = \frac{K \cdot \max_j \|\delta_j(\hat{x}_m)\|_1 / \|\hat{x}_m\|_1 - 1}{K - 1} \in [0, 1] \tag{9}$$

The SCI measures how concentrated the coefficients are in the dictionary. $SCI(\hat{x}_m)=1$, if the test vector can be strictly linearly represented using training vectors from only one class; and $SCI(\hat{x}_m)=0$, if the coefficients are spread evenly over all classes. The weight of $\hat{x}_m$ is obtained by normalizing the SCIs among the obtained M gait cycles:

$$\alpha_m = SCI(\hat{x}_m) \Big/ \sum_{n=1}^{M} SCI(\hat{x}_n) \tag{10}$$

At 668, with the knowledge of $\hat{x}_{sum}$, the compressed residual of each class is computed as:

$$r_i(y_{sum}) = \|R_{opt}y_{sum} - R_{opt}A\delta_i(\hat{x}_{sum})\|_2 \tag{11}$$

where $y_{sum} = \sum_{m=1}^{M} \alpha_m y_m$ is the weighted summation of all the test vectors. The final identity 670 is obtained by finding the minimal residual.

Figure 7B:
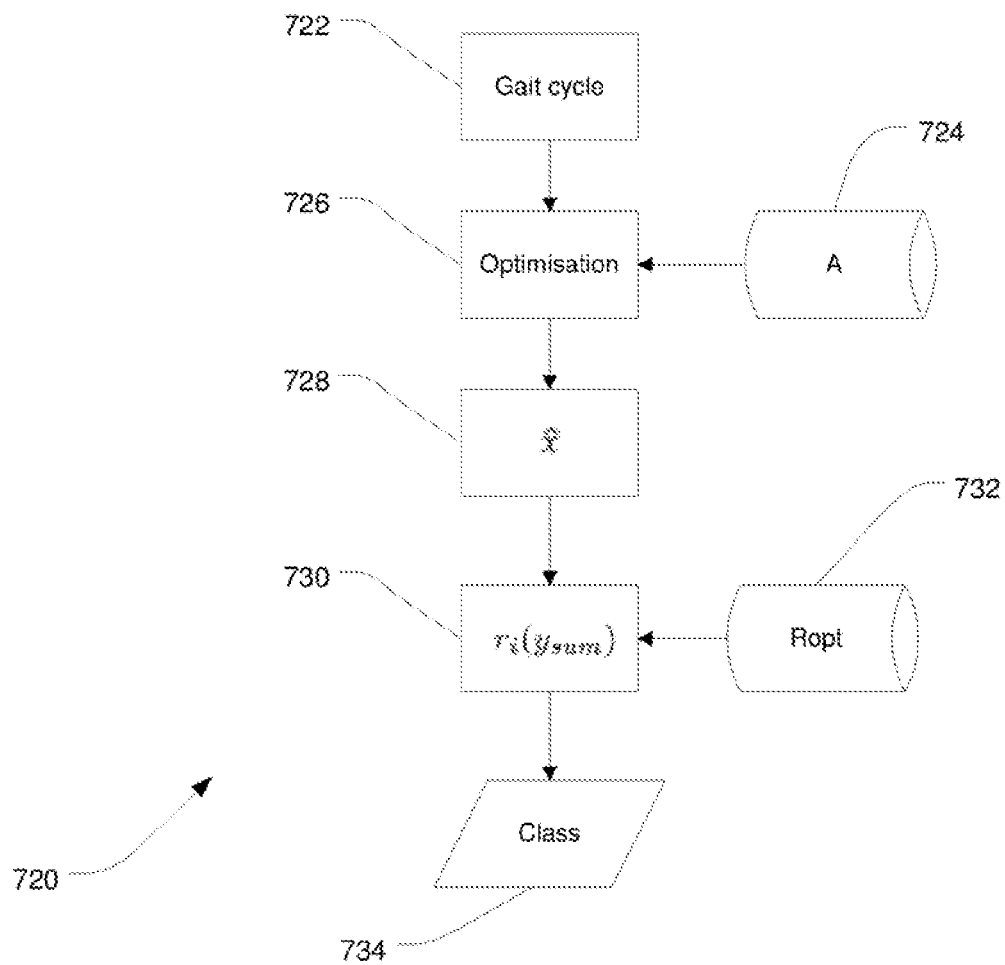
FIG. 7b is a flow diagram of classification using a sparse fusion model.

FIG. 7b provides an overview of the sparse fusion classification method 720. At 722 one or more gait cycles are received or determined. At 726 these gait cycles are optimised using $l_1$ optimisation to determine the coefficients vector $\hat{x}$. This step uses the dictionary A 724 that was built during a separate the dictionary training stage 600. A sparse representation model, $\hat{x}$, is determined at 728. $\hat{x}$ is then used, together with the optimal projection matrix $R_{opt}$ (also determined during the training stage 600) to calculate the minimal residual at 730. The output 734 of this process is the classification.

It has been shown that this proposed sparse fusion method is up to 10% more accurate than other classification methods such as Naïve Bayes.

The description above has focused on human activity recognition with examples relating to characteristics of human activity. In that respect the relevant sensing pertains to human activities, and the type of energy used for energy harvesting for these examples is kinetic energy. The system and methods described herein can be extended to other applications, for example structural health monitoring where harvested kinetic energy from the movement and/or vibration of structures such as buildings or bridges provides an indication of structural health or changes in structural health over time.

The system and methods described herein can also be extended to other types of sensed phenomena where energy may be harvested from the relevant environment in a different form. For example, a temperature sensor arrangement may be powered by harvested heat energy. In a comparable way the characteristics of the harvested heat energy may be used to indicate characteristics of the heat source such as the temperature.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An energy harvesting system comprising:
a transducer that generates an electric signal from ambient energy;
a power conditioning circuit to rectify and regulate the electric signal to produce a regulated electric signal;
an energy storage to store the regulated electric signal and provide power to the processor and a transmitter; and
a processor adapted to process the electric signal to determine a characteristic of a source of the ambient energy that is associated with a user's gait and is indicative of a user's identification by:
obtaining gait cycle vectors from the electric signal;
estimating a set of coefficients vectors by optimizing the gait cycle vectors using a predetermined dictionary;
generating a sparse fusion model by combining the set of coefficients vectors;
determining a minimal residual using the sparse fusion model and a projection matrix; and
determining the characteristic using the minimum residual, and to output the characteristic.

2. The system of claim 1 wherein the gait cycle vectors are obtained by segmenting the electrical signal by gait cycles to provide a plurality of gait cycle vectors.

3. The system of claim 2 wherein combining the estimated coefficients vectors to reduce noise comprises generating a weighted sum of the estimated coefficients vectors.

4. The system of claim 3 wherein the weight for a given estimated coefficients vector is found by normalizing a sparsity concentration index calculated for that estimated coefficients vector.

5. The system of claim 2 wherein the projection matrix is an optimal projection matrix produced using a heuristic algorithm.

6. The system of claim 1 wherein optimizing the gait cycle vectors comprises using $l_1$ optimization and the predetermined dictionary.

7. A method for determining a characteristic of a source of ambient energy that is associated with a user's gait and is indicative of a user's identification, the method comprising:
receiving and transforming ambient energy into an electrical signal;
rectifying and regulating the electric signal by a power conditioning circuit to produce a regulated electric signal;
storing the regulated electric signal in an energy storage to provide power to the processor and a transmitter;
obtaining gait cycle vectors from the electric signal;
estimating a set of coefficients vectors by optimizing the gait cycle vectors using a predetermined dictionary;
generating a sparse fusion model by combining the set of coefficients vectors;
determining a minimal residual using the sparse fusion model and a projection matrix;
determining the characteristic using the minimum residual, and outputting the characteristic.

8. The method of claim 7 wherein the gait cycle vectors are obtained by segmenting the electrical signal by gait cycles to provide a plurality of gait cycle vectors.

9. The method of claim 8 wherein combining the estimated coefficients vectors to reduce noise comprises generating a weighted sum of the estimated coefficients vectors.

10. The method of claim 9 wherein the weight for a given estimated coefficients vector is found by normalizing a sparsity concentration index calculated for that estimated coefficients vector.

11. The method of claim 7 wherein the projection matrix is an optimal projection matrix produced using a heuristic algorithm.

12. The method of claim 7 wherein optimizing the gait cycle vectors comprises using $l_1$ optimization and the predetermined dictionary.

* * * * *